United States Patent

Ronnquist

[11] 4,030,500
[45] June 21, 1977

[54] FECAL MATTER COLLECTOR

[76] Inventor: Hadar Yngve Ronnquist, 95082 Nikkala, Sweden

[22] Filed: Dec. 5, 1975

[21] Appl. No.: 638,033

Related U.S. Application Data

[63] Continuation of Ser. No. 518,952, Dec. 16, 1974, abandoned.

[52] U.S. Cl. .............................................. 128/283
[51] Int. Cl.² .......................................... A61F 5/44
[58] Field of Search ................... 128/283, 246, 129

[56] References Cited

UNITED STATES PATENTS

| 2,765,790 | 10/1956 | Dickson | 128/283 |
|---|---|---|---|
| 2,874,697 | 2/1959 | Johnson | 128/283 |
| 3,548,828 | 12/1970 | Vasile | 128/283 |
| 3,802,418 | 4/1974 | Clayton | 128/283 |
| 3,938,521 | 2/1976 | Ritota et al. | 128/283 |

Primary Examiner—John D. Yasko
Attorney, Agent, or Firm—Sixbey, Bradford & Carlson

[57] ABSTRACT

A Fecal Matter Collector including a tubular portion of flexible material having a portion operatively associated with a user's rectum and another portion extending through the anal opening and having on the external end thereof a removable collecting bag, and including a gas escape outlet.

1 Claim, 1 Drawing Figure

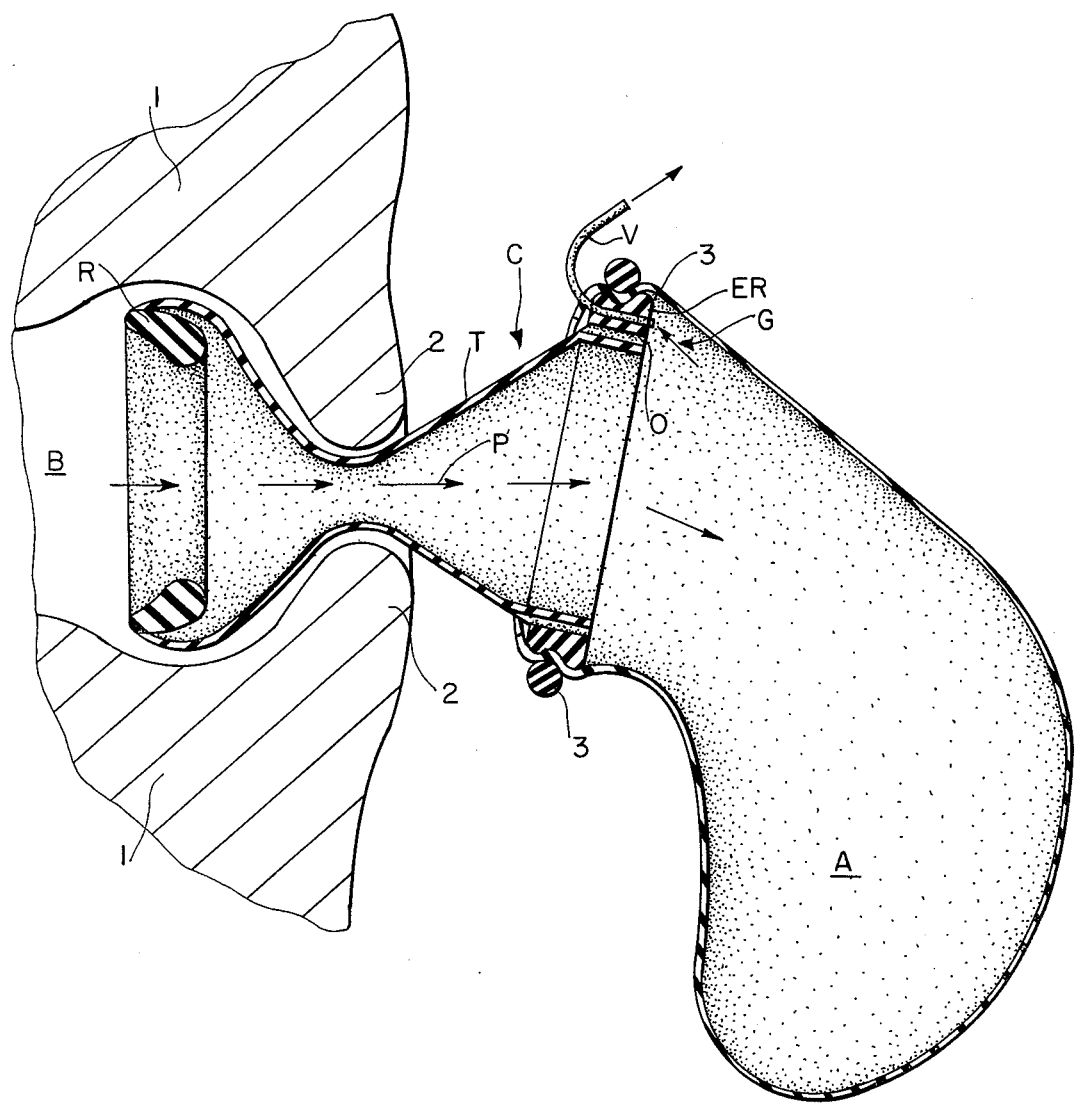

FECAL MATTER COLLECTOR

This is a continuation of application Ser. No. 518,952, filed Dec. 16, 1974, now abandoned.

BACKGROUND OF THE INVENTION

As is known, bed-ridden, sick or infirm persons and the like pose problems for collection and disposal of fecal matter and the like, the patient being unable to utilize normal toilet facilities external of the bed, and the usual known bedpans in many instances are not convenient in use and are objectionable in many respect to the user and assisting personnel.

Attempts have heretofore been made to overcome this problem and to provide a device such as a fecal matter collector which is readily adaptable to a patient, comfortable in use, easy for placement in or removal from an operative position and to otherwise generally eliminate cumbersome, difficult to operatively place and/or remove, uncomfortable in use and expensive items. An example of such a device is shown in the patent to Vasile, U.S. Pat. No. 3,548,828, issued Dec. 22, 1970. This device which constitutes known prior art does not satisfy the requirements and desired factors which have been long outstanding.

The present invention is devised to overcome the known drawbacks.

BRIEF DESCRIPTION OF THE INVENTION

A fecal matter collector especially adapted for use by bedridden, sick or infirm persons and the like, and generally consisting of a flexible and resilient tubular first portion, one end of which is insertable into an operative position interior of a patient and in association with the rectum of a user, the other end being external of the anal opening, with an intermediate constricted portion disposed in and through the anal sphincter, and a resilient collecting bag removably attached to the external end, provision being made for escape of gases from the collecting bag.

Additional features, objects and advantages of the present invention will be more readily apparent from the accompanying drawing in which the single FIG. is a pictorial representation, partly in elevation and partly in section, showing the invention as operatively associated with a patient.

Referring now more specifically to the drawing, there is shown a fecal matter collector operatively associated with a user to collect fecal discharges from, for example, sick or infirm persons who are unable to use normal toilet facilities or other sanitary receptacles. A portion of the buttocks of a user is shown is also, generally designated, the rectum B of the user as also the anal outlet therefrom. The anal outlet includes, as is well known, an anal sphincter muscle at the position generally designated 2 in the drawing at which position the rectum of the person opens to the exterior.

Basically, the collector of the present invention consists of an open-ended tubular elastomeric member with one end thereof adapted for insertion into a person's anus, with the end thereof terminating in a resilient ring attached or integrated with the end by any known means. The collector further includes a central portion which is narrowed or constricted where it is intended to pass through the anal sphincter and on the external end a second ring is adapted for removable association therewith of the removable fecal matter collector bag.

Again referring specifically to the drawing, the sack A adapted for collecting the fecal matter is constituted of, preferably, thin plastic material having an open end to which is associated a ring 3 of rubber or plastic and which is preferably removably or attached to the opening. This ring generally is of a flattened conical configuration and includes a groove in the outer periphery thereof which is mated with the interior portion of the bag A at its opening. In some constructions it is found desirable that the resilient collecting bag A be made separable from the remainder of the structure for cleaning and/or replacement as desired. To this end, a flexible and stretchable ring is placed externally of the opening of the bag and in co-action with the groove of the ring 3 removably attaches the bag to the ring 3.

A generally tubular portion or member T extends through the anal opening into a co-acting position with respect to the rectum of a user and this member T has a constricted portion where it passes through the sphincter muscle of the user at 2. The internal end of this tubular member has incorporated therein or attached thereto, preferably adhesively or by welding or the like, a ring designated R which is of resilient, flexible and stretchable material and which, as will be noted from the drawing, is of a generally flattened conical configuration for better and more comfortable association with the internal areas of a user at the rectum.

The external ring designated ER is also preferably of the same nature and general shape as the ring R and is affixed to the tube T adjacent its external open end in the same manner. There is additionally provided at the connection of ring ER with tube T, or preferably within the material of the ring itself, air outlet or opening generally designated O which permits gases or air to escape from the bag A for obvious reasons.

The tube T and inner ring R and outer ring ER are compositely identified by the letter C.

Arrows disignated P indicate flow of fecal matter from the rectum of a user through the tube T into the bag A. The passage or venting of gases of air are generally designated by the arrows at G and this structure can include either an opening to the exterior or a vent tube or the like generally designated at V.

It will be seen that for use the device is operatively associated with a patient or user with the inner end of the thin rubber tube T and ring R being passed through the anal opening and positioned by means of ring R within the rectum. The constricted portion of the tube is associated with the anal sphincter at 2 and the material and construction is such, the tube being of a soft plastic or the like, that when an evacuation occurs from the rectum B, the restricted or constricted portion can open or expand so that the material discharged through the tube C and outer ring ER will pass into the collecting bag A. Gases or air will vent from this bag and overall the usage of the device is as comfortable to the user and as effective as is possible, many inconveniences and discomfort being eliminated as compared with known devices.

It will be noted that the internal ring R serves to maintain the tube T in place in the rectum in such a manner, due to the configuration and material used, that the tube cannot be dislodged by force without collapsing the ring and pulling the tube out of the rectum or anal cavity. The material is also such that no interference occurs with fecal matter being evacuated.

The bag can be easily and readily removed for cleaning or replacement by a new one.

Manifestly changes of a minor nature can be effected in the structure without departing from the spirit or scope of the invention as defined in and limited solely by the appended claims.

I claim:

1. A fecal matter collector including a continuous closed tubular member of flexible and resilient material having a first end operatively associated with a user's rectum, said first end being inserted within the rectum, said member having an intermediate length of restricted cross section placed at and extending through the anal opening of a user at the place of the sphincter muscle of the user, a second end of said member external of the rectum, said ends being of substantially greater dimensions than that of said restricted intermediate length and being open, a solid ring of resilient material operatively connected with each said open end of the tubular member and conjointly therewith forming the overall continuous closed tubular member, said ring at the internal end of said member being attached in the interior of the tube at the open end, and having a flattened conical configuration for association with the interior of the rectum proximate the anal opening and anal sphincter thereof, and adapted for maintaining the tube in operative association within the rectum of a user, a collector bag of substantially uniform resilient and continuous material, said bag having an open end and being removably connected to said second external end of said tubular member, the external ring being integrated with the exterior of the tube material proximate the second open end and having an external groove therein, said collector bag having the open end thereof positioned externally of said ring, and a resilient material solid ring disposed externally of the end of the bag, and associating this end in the groove of the ring and resiliently interconnecting the collector bag with the tubular member and adapting the bag for easy removal for cleaning and/or replacement, and at the external ring a gas and air vent opening to permit escape of gaseous material from the collecting bag to the exterior.

* * * * *